United States Patent [19]

Drury et al.

[11] Patent Number: 4,851,569
[45] Date of Patent: Jul. 25, 1989

[54] CONTINUOUS PROCESS FOR THE PRODUCTION OF METHYL FORMATE BY THE CHROMIUM CATALYZED LIQUID PHASE OXIDATION OF METHANOL

[75] Inventors: David J. Drury, Hedon; John Pennington, Willoughby, both of England

[73] Assignee: BP Chemicals Limited, London, England

[21] Appl. No.: 741,193

[22] Filed: Jun. 4, 1985

Related U.S. Application Data

[63] Continuation of Ser. No. 565,512, Dec. 27, 1983, abandoned, which is a continuation of Ser. No. 357,864, Mar. 17, 1982, abandoned.

[30] Foreign Application Priority Data

Mar. 17, 1981 [GB] United Kingdom ............... 8108351
Mar. 17, 1981 [GB] United Kingdom ............... 8108310

[51] Int. Cl.$^4$ .................... C07C 67/40; C07C 69/06
[52] U.S. Cl. .................... 560/239; 562/538; 568/594
[58] Field of Search ........................ 560/239

[56] References Cited

U.S. PATENT DOCUMENTS 4,126,748 11/1978 Scholz et al. ............... 560/239

Primary Examiner—Vivian Garner
Attorney, Agent, or Firm—Brooks Haidt Haffner & Delahunty

[57] ABSTRACT

Methyl formate is produced continuously by reacting methanol in the liquid phase with molecular oxygen in the presence as catalyst of a soluble chromium compound which can be deliberately added or can result from corrosion of a reaction vessel fabricated in stainless steel or other chromium-containing metal alloy. Initiation of the oxidation can be accomplished by feeding a material more susceptible to oxidation than methanol, either with or without methanol, and optionally in the presence of a soluble chromium compound.

13 Claims, 1 Drawing Sheet

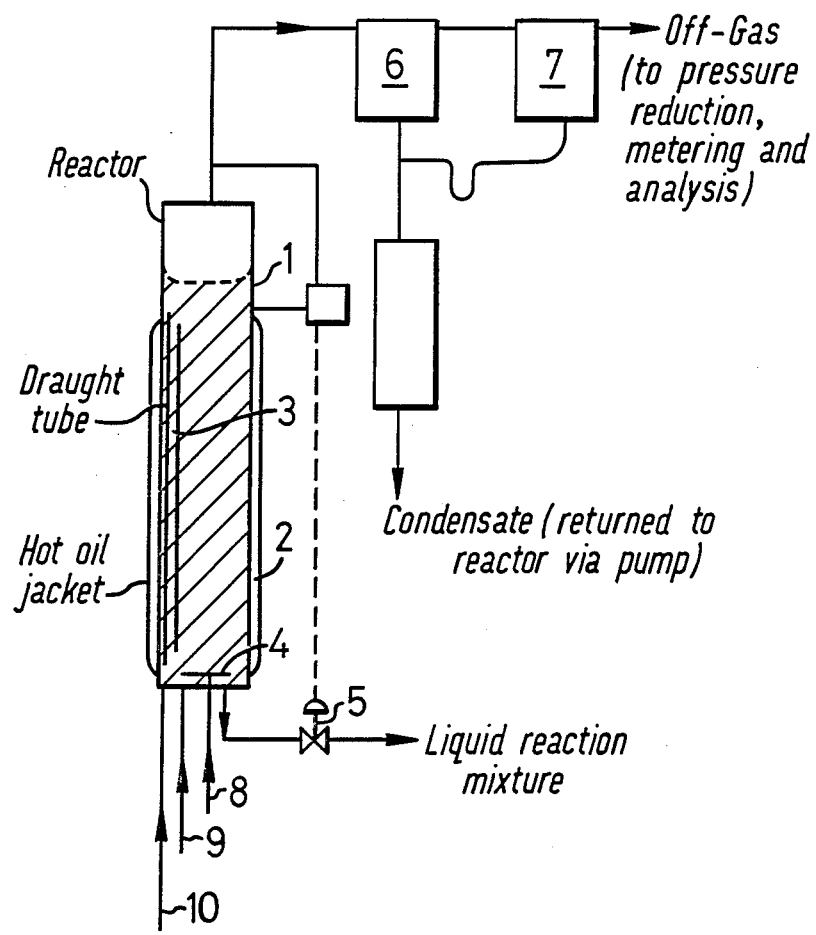

CONTINUOUS PROCESS FOR THE PRODUCTION OF METHYL FORMATE BY THE CHROMIUM CATALYZED LIQUID PHASE OXIDATION OF METHANOL

This application is a continuation of application. Ser. No. 565,512, filed 12/27/83, now abandoned, which is a continuation of application Ser. No. 357,864, filed 3/17/82, now abandoned.

The present invention relates to a continuous process for the production of methyl formate by the liquid phase oxidation of methanol.

In recent years formic acid has assumed some importance in agriculture, particularly as a silage additive and preservative. One source of formic acid has been as a by-product in the production of acetic acid by the oxidation of paraffinic hydrocarbon feedstocks. With the advent of processes producing exclusively acetic acid by the carbonylation of methanol a need has arisen for a process for producing formic acid to satisfy the market demand. One of the possible routes to formic acid is the hydrolysis of methyl formate.

U.S. Pat. No. 4,126,748 describes a process for the production of carboxylic acid esters by catalytic oxidation in the liquid phase of a primary straight chain alcohol or a mixture of such alcohols, or a mixture of an aldehyde and a primary straight chain alcohol, each of 1-4 carbon atoms, with molecular oxygen at elevated temperatures in the presence of a catalyst which is a solution in the liquid phase of (a) a compound of Co, Mn, Cr, or Fe, and (b) an acid having a first dissociation constant $K_1$ greater than $10^{-3}$. When the alcohol is methanol, the product is methyl formate. Suitable acids having a dissociation constant $K_1$ greater than $10^{-3}$ are said to be inorganic acids, including HCl, $HNO_3$, $HClO_4$, $H_2SO_4$, $HBr, H_3PO_4$, HI, etc and organic acids such as methanesulphonic acid, p-chlorobenzoic acid, oxalic acid, trichloroacetic acid etc. The metal compounds are said to be catalytically active in extremely minor amounts, a concentration of 0.2 to 100 ppm, calculated as the metal, generally being employed. It is stated that catalytically active metal concentrations may arise from corrosion of the reactor material, even in vessels made of stainless steel.

We have now found that in the presence of a chromium catalyst methanol can be continuously oxidised to methyl formate in the absence of an acid having a first dissociation constant $K_1$ greater than $10^{-3}$. Furthermore, we have found that when the process is carried out in a stainless steel reaction vessel in the absence of such an acid, even the very low concentrations of soluble chromium compounds arising from corrosion of the vessel provide significant rates of oxidation.

Accordingly, the present invention provides a process for the continuous production of methyl formate by continuously reacting methanol in the liquid phase with molecular oxygen at elevated temperature in the presence of an oxidation catalyst, characterised in that as the oxidation catalyst there is used a soluble chromium compound.

Methanol is a readily available industrial product which is generally manufactured from synthesis gas, i.e. mixtures of carbon monoxide and hydrogen. It is preferred to use substantially anhydrous methanol, though water may be present in an amount up to 20% w/w.

The molecular oxygen may suitably be fed in the form, for example, of air or mixtures of gases richer or poorer in molecular oxygen than air.

Suitable soluble chromium compounds include salts, wherein the metal is present either as the anion, e.g. sodium dichromate, or as the cation, e.g. the nitrate, sulphate and chloride, complexes and other metal compounds, e.g. chromium trioxide. The chromium compound may be present in an amount in the range 0.05 to 100 ppm, preferably in the range 0.5 to 10 ppm, calculated as the metal and based on the amount by weight of the methanol fed. The chromium compound may be deliberately added or may arise from corrosion in the event that the reaction vessel in which the oxidation is carried out if fabricated in stainless steel or other chromium containing metal alloy. Suitably the chromium compound is fed in the form of an aqueous or methanolic solution.

The elevated temperature may suitably be in the range 50° to 250° C., preferably in the range 100° to 200° C. The pressure employed must be that pressure or greater which is sufficient to maintain the reaction mixture in the liquid phase at the prevailing reaction temperature.

The process may be carried out in any of the known types of apparatus for effecting gas/liquid reactions. An example of a suitable form of apparatus is a vertical tower containing a coaxial draught tube open at both ends thereof. The tower is continuously filled to at least the height of the top of the draught tube with liquid reactant, gas is introduced through a sparger located near the base and external to the draught tube. The mixture of gas and liquid rises until it is level with the top of the draught tube, whereupon the gas disengages from the liquid and the liquid descends through the draught tube to the base of the reactor, thereby establishing continuous circulation of the reaction mixture. Liquid containing reaction products is removed from the base region of the tower at a rate commensurate with the maintenance of a constant liquid level in the tower. Optionally, a portion of the condensate may be recovered and separated into liquid products. Provision is also made for feeding catalyst and recycle streams and removing gases overhead. The apparatus may suitably be fabricated in stainless steel or titanium.

The continuous oxidation may be initiated by a variety of methods. In order to avoid prolonged induction periods before the onset of oxidation it is preferred to initiate the oxidation reaction by initially charging, in the presence or absence of methanol, material(s) which (is) are more susceptible to oxidation than methanol alone and, after the onset of oxidation, feeding methanol in the absence of material more susceptible to oxidation. Thus oxidation may be initiated by initially charging a paraffinic hydrocarbon. The paraffinic hydrocarbon is preferably a paraffin containing from 4 to 8, even more preferably from 5 to 7 carbon atoms in the molecule, or a mixture of such paraffins. The paraffin may be straight-chain paraffin, used either alone or in admixture with branched-chain and cyclic paraffins. Paraffinic fractions may suitably by employed, particularly those boiling at a temperature not exceeding 100° C. It is particularly preferred to use a fraction having a boiling range of about 15° to about 95° C. Alternatively, oxidation may be initiated by charging the product of a previous methanol oxidation or a synthetic composition corresponding to such a product, optionally with the introduction of additional methanol. Other compounds which are more susceptible to oxidation than methanol and which may be used as, or added to methanol or the product of a previous methanol oxidation in the initial charge are, for example, ethanol and 2-butanone. Preferably initiation is effected in the presence of a soluble chromium compound. The soluble chromium compound is preferably present as an oxidation initiator at a higher concentration, e.g. up to 200 ppm, that that employed during the subsequent continuous methanol oxidation reaction.

In addition to methyl formate there may be formed varying proportions of side-products such as dimethoxymethane (the acetal formed by reaction of formaldehyde with methanol), water, formaldehyde and formic acid. After separation of methyl formate from the liquid product by, for example distillation, it may be desirable to recycle some at least of the side-products remaining together with unreacted methanol and the catalyst to the methanol oxidation process. Alternatively dimethoxymethane for example may be recovered.

As mentioned hereinbefore one of the principal uses of methyl formate is its conversion by hydrolysis to formic acid.

Accordingly, another aspect of the present invention provides a process for the production of formic acid by hydrolysing methyl formate characterised in that the methyl formate is produced by the process as hereinbefore described.

Many processes for hydrolysing methyl formate are known in the art. Representative of such art is U.S. Pat. No. 3,907,884; GB No. 1490374; Norwegian Pat. No. 138,803; EP No. 5998; DT No. 2774313; U.S. Pat. Nos. 2,160,064; 2,286,407; 2,373,583; DS No. 639064 and GB No. 628656. The methyl formate may be hydrolysed by the processes described in any of the aforesaid patent specifications.

The invention will now be described by reference to the following Examples. In the Examples use was made of the apparatus illustrated in the accompanying FIGURE. With reference to the FIGURE, 1 denotes a reaction vessel fabricated in stainless steel, approximately 1.5 m in height and 10 cm inner diameter; 2 is a heating oil jacket; 3 is a "draught tube" of segmental cross-section, its purpose being to promote circulation of the reactor contents; 4 is an air distributor; 5 is a level-controlled liquid release valve; 6 is a water-cooled condenser; 7 is a refrigerated condenser cooled with aqueous methanol; 8 is an air inlet pipe; 9 is a combined methanol and liquid recycle inlet pipe and 10 is a combined catalyst solution feed and condensate return pipe.

EXAMPLE 1

Initiation of oxidation using chromium, and subsequent continuous operation with a chromium catalyst (5 ppm), without recycle of by-products.

The reactor was charged with the product from a previous methanol oxidation reaction, together with sufficient sodium dichromate to give 25 ppm by weight of Cr in the mixture.

The reactor was then pressurised to 49 bar (abs) with nitrogen, and the mixture heated to a temperature of 175° C. Air was then introduced through pipe 8 at a rate of approximately 3 kg h$^{-1}$. Oxidation commenced almost immediately, as indicated by the oxygen content of the off-gases. Liquid feeds to the reactor through pipes 9 and 10 were then started, and the reaction temperature adjusted to its desired value. The air feed rate was adjusted to maintain the desired oxygen content in the off-gases, and liquid products were withdrawn through valve 5 at a rate sufficient to maintain a constant liquid level in the reactor.

Several hours after the initiation of the reaction the reactor was operating continuously under the following conditions:

Reaction temperature: 192° C.
Air feed-rate: 8289 g h$^{-1}$
Oxygen content of off-gases: 3.9% v/v
Methanol feed-rate: 6233 g h$^{-1}$
Catalyst feed rate (0.3% w/w Na$_2$Cr$_2$O$_7$ soln.).: 30 ml h$^{-1}$
Liquid product withdrawal rate: 6902 g h$^{-1}$
Liquid product composition (% w/w)
Methanol: 42.2
Methyl formate: 23.2
Dimethoxymethane: 8.4
Water: 21.2
Formic acid: 5.0

EXAMPLE 2

Initiation of oxidation using chromium, and subsequent continuous operation with a chromium catalyst (5 ppm Cr), with partial recycle of by-products.

The reaction vessel was charged with a product from a previous methanol oxidation reaction, together with sufficient sodium dichromate to give 20 ppm by weight of Cr in the mixture. The reaction was initiated in the mixture using the procedure indicated in Example 1.

The procedure of Example 1 was then followed except that the liquid product removed through valve 5 was fed to the mid-point of a first distillation column approximately 3m in height and 10 cm internal diameter packed with 10 mm ceramic Raschig rings and provided with an electrically heated metal reboiler. Removed from the base of the column was a fraction containing methanol, water, catalyst and formic acid. The head product from the first column was divided into two parts, one of which was re-introduced to the head of the column as reflux, the other being fed to a second column at a point 1.5 m from its base. The second column was 3.7 m in height and 7.6 cm inner diameter. This column was packed with 10 mm ceramic Raschig rings and also provided with an electrically heated metal reboiler. The head product from the second column contained greater than 90% by weight methyl formate. This stream was divided into two parts, one of which was returned to the head of the column as reflux, the other being continuously withdrawn as crude methyl formate product. The base product from the second column consisted substantially of dimethoxymethane and methanol. This stream was recycled to the reactor through pipe 9 together with fresh methanol.

Several hours after initiation of the oxidation reaction the reactor was operating continuously under the following conditions:

Reaction temperature: 191° C.
Air feed rate: 7178 g h$^{-1}$
Oxygen content of off-gases: 3.7% v/v
Methanol feed-rate: 6260 g h$^{-1}$
Catalyst feed-rate (0.3% w/w aq. Na$_2$Cr$_2$O$_7$soln.): 30ml h$^{-1}$
Recycle feed rate: 565 g h$^{-1}$

RECYCLE COMPOSITION (% w/w)

Methanol: 13.9
Methyl formate: 24.3
Dimethoxymethane: 61.7
Water: 0.1

Reactor product withdrawal rate: 7268 g h$^{-1}$

REACTOR PRODUCT COMPOSITION (% w/w)

Methanol: 44.0
Methyl formate: 23.3
Dimethoxymethane: 8.8
Water: 20.6
Formic acid: 3.4

EXAMPLE 3

Initiation of oxidation using chromium, and subsequent continuous operation with a chromium catalyst (50 ppm, Cr) with partial recycle of by-products.

The initiation procedure described in Example 1 was followed. Thereafter the procedure described in Example 2 was repeated except that the concentration of chromium in the reaction mixture was increased to 50 ppm.

Several hours after initiating the oxidation the reactor was operating continuously to the following conditions:
Reaction temperature: 191° C.
Air feed-rate: 8285 g h$^{-1}$
Oxygen content of off-gases: 4.3% v/v
Methanol feed-rate: 6262 g h$^{-1}$
Catalyst feed rate (3% w/w aq Na$_2$Cr$_2$O$_7$ soln): 30ml h$^{-1}$
Recycle feed-rate: 535 g h$^{-1}$ RECYCLE COMPOSITION (% w/w)

Methanol: 16.0
Methyl formate: 14.5
Dimethoxymethane: 69.5
Reactor product withdrawal rate: 7716 g h$^{-1}$ REACTOR PRODUCT COMPOSITION (% w/w)

Methanol: 43.8
Methyl formate: 22.1
Dimethoxymethane: 8.3
Water: 22.3
Formic acid: 3.5

EXAMPLE 4

Initiation of oxidation using naphtha, and subsequent continuous operation in the absence of naphtha, with no by-product recycle.

With reference to the FIGURE reactor 1 was charged with 7 liters of product from an earlier naphtha oxidation, comprising lower carboxylic acids, water, hydrocarbons and ester/ketone oxidation intermediates, together with 3 liters of additional naphtha. The reactor was then pressurised to 49 bar (abs). with nitrogen, and the mixture heated to a temperature of 175° C. Air was then introduced through pipe 8 at a rate sufficient to maintain the oxygen concentration in the off-gases at about 1% v/v, while naphtha was fed through pipe 9 at a rate of 1 kgh$^{-1}$.

Methanol feed was then introduced and the methanol feed-rate gradually increased to the desired value. As methanol is less readily oxidised than naphtha it was necessary to gradually increase the reaction temperature as the ratio of the methanol feed-rate to the naphtha feed-rate increased. The desired methanol feed-rate having been arrived at, the naphtha feed-rate was gradually reduced to zero.

Several hours after discontinuing the naphtha feed, the reaction conditions were was follows:
Reaction temperature: 190° C.
Air feed-rate: 1885 g h$^{-1}$
Oxygen content of off-gases: 0.1% v/v
Methanol feed-rate: 2771 g h$^{-1}$
Liquid product withdrawal rate: 3087 g h$^{-1}$ LIQUID PRODUCT COMPOSITION (% w/w)

Methanol: 54.3
Methyl formate: 19.7
Dimethyoxymethane: 7.5
Formic acid: 2.8
Water: 15.5

METAL ION CONCENTRATION IN LIQUID PRODUCT (ppm by wt.)

Iron: 0.4
Nickel: 0.4
Chromium: 0.1

EXAMPLE 5

Initiation of oxidation using chromium, subsequent continuous operation in the absence of chromium, with partial recycle of by-products.

The reactor 1 was charged with the product from a previous methanol oxidation reaction, together with sufficient sodium dichromate to give 25 ppm by weight of Cr in the mixture.

The reactor was then pressurised to 49 bar (abs) with nitrogen, and the mixture heated to a temperature of 175° C. Air was then introduced through pipe 8 at a rate of approximately 3 kg. h$^{-1}$. The oxidation commenced almost immediately, as indicated by the oxygen content of the off-gases. Liquid feeds to the reactor free from catalytic metal compounds were then started, and the reaction temperature adjusted to its adjusted value. The air feed rate was adjusted to maintain the desired oxygen content in the off-gases, and liquid products were withdrawn through valve 5 at a rate sufficient to maintain a constant liquid level in the reactor. in this Example the liquid product removed through valve 5 was fed to the mid-point of a first distillation column approximately 3m in height and 10 cm internal diameter packed with 10 mm ceramic Raschig rings and provided with an electrically heated metal reboiler. Removed from the base of the column was a fraction containing methanol, water and formic acid. The head product from the first column was divided into two parts, one of which was re-introduced to the head of the column as reflux, the other being fed to a second column at a point 1.5 m from its base. The second column was 3.7 m in height and 7.6 cm inner diameter. This column was packed with 10 mm ceramic Raschig rings and also provided with an electrically heated metal reboiler. The head product from the second column contained greater than 90% by weight methyl formate. This stream was divided into two parts, one of which was returned to the head of the column as reflux, the other being continuously withdrawn as crude methyl formate product. The base product from the second column consisted substantially of dimethoxymethane and methanol. This stream was recycled to the reactor through pipe 9 together with fresh methanol.

Several hours after initiation of the oxidation reaction the reactor was operating continuously under the following conditions:
Reaction temperature: 188.4° C.
Air feed-rate: 6826 g h$^{-1}$
Oxygen content of off-gases: 3.4% v/v
Methanol feed-rate: 6310 g h$^{-1}$
Recycle stream feed-rate: 341 g h$^{-1}$

COMPOSITION OF RECYCLE STREAM (% w/w)

Methanol: 22.9
Dimethoxymethane: 60.6
Methyl Formate: 16.2
Water: 0.3
Rate of withdrawal of reactor product: 7475 g h$^{-1}$

COMPOSITION OF REACTOR PRODUCT (% w/w)

Methanol: 48.4
Dimethoxymethane: 6.3
Methyl formate: 23.9
Water: 18.2
Formic acid: 3.2

Concentrations of metal ions in the liquid product were similar to those quoted in the preceding Example i.e. iron (0.4 ppm), nickel (0.4 ppm) and chromium (0.1 ppm).

Examples 4 and 5 demonstrate that the very low concentrations of chromium ions arising from corrosion of the stainless steel reaction vessel are sufficient to maintain the continuous oxidation of methanol in the absence of deliberately added chromium.

EXAMPLE 6

The purpose of this Example is to compare the oxidation rates achieved by the use of a chromium-containing catalyst with those obtained in the absence of a catalyst and in the presence of additives other than chromium. Insofar as the Example relates to an uncatalysed reaction and reations in which additives other than chromium are used it is not an example illustrating the invention.

After initiation of the oxidation a series of experiments was carried out with different additives. Several hours were allowed to elapse after the additive had been changed and before measurement of the oxidation rate was commenced.

For each experiment, methanol was fed to the reactor at ca. 6200 g h$^{-1}$. The reaction temperature was maintained at 189°±2° C. and air was fed at a rate sufficient to maintain an oxygen concentration of ca. 4% v/v in the off-gases. Partial recycle of by-products was carried out as exemplified in Examples 2 and 3. The various metal compound additives were fed to the reactor as aqueous solutions of a concentration calculated to give the required metal concentration in the reactor when introduced at a rate of 30ml h$^{-1}$.

The results of these experiments are indicated in the following Table:

TABLE

| Reaction Additive | Additive Concentration (ppm by weight of transition metal in reactor) | Oxygen Absorption Rate (mol h$^{-1}$) |
| --- | --- | --- |
| Na$_3$VO$_4$ | 10 | 23 |
| Na$_2$MoO$_4$ | 10 | 45 |
| Ni(CH$_3$CO$_2$)$_2$ | 10 | 46 |
| None | — | 48 |
| Mn(CH$_3$CO$_2$)$_2$ | 10 | Too low for stable measurement |
| Co(CH$_3$CO$_2$)$_2$ | 10 | 47 |
| Fe(NO$_3$)$_3$ | 10 | 41 |
| Na$_2$WO$_4$ | 10 | 41 |
| Na$_2$Cr$_2$O$_7$ | 5 | 59 |

The results presented in the Table demonstrate that the oxidation rate as measured by the oxygen absorption rate achieved using vanadium, molybdenum, nickel, manganese, cobalt, iron and tungsten is either comparable with or less than the rate attainable without deliberate addition of a reaction additive when such oxidation is carried out in a stainless steel vessel. Only by the addition of chromium is a substantial increase in the methanol oxidation rate achieved.

We claim:

1. A process for the continuous production of methyl formate which comprises continuously reacting methanol in the liquid phase with molecular oxygen at elevated temperature in the range of 50° to 250° C. in the presence of a soluble chromium compound oxidation catalyst and in the absence of an acid having a first dissociation constant K, greater than 10$^{-3}$.

2. A process according to claim 1 wherein the molecular oxygen is fed in the form of air.

3. A process according to claim 1 or claim 2 wherein the chromium compound is present in an amount in the range 0.05 to 100 ppm calculated as the metal and based on the amount by weight of the methanol fed.

4. A process according to claim 3 wherein the chromium compound is present in the range 0.5 to 10 ppm.

5. A process according to wherein the reaction vessel is fabricated in stainless steel or other chromium-containing alloy and the chromium catalyst arises from corrosion of the reaction vessel.

6. A process according to claim 3 wherein the elevated temperature is in the range 100° to 200° C.

7. A process according to claim 1 wherein the material more susceptible to oxidation is a paraffinic hydrocarbon.

8. A process according to claim 9 wherein the paraffinic hydrocarbon is a fraction having a boiling range of 15° to 95° C.

9. A process according to claim 1 wherein the material more susceptible to oxidation is the product of a previous methanol oxidation or a synthetic composition corresponding to such a product.

10. A process according to claim 1 wherein the material more susceptible to oxidation is either ethanol or 2-butanone.

11. A process as defined in claim 1 wherein the reaction is initiated by initially charging, in the presence or absence of the methanol, a material which is more susceptible to oxidation than the methanol selected from the group consisting of a paraffinic hydrocarbon, the product of a previous methanol oxidation, a synthetic composition corresponding to said product, ethanol, and 2-butanone.

12. A process as claimed in claim 11 wherein the initiation is effected in the presence of a soluble chromium compound.

13. A process as claimed in claim 12 wherein the concentration of soluble chromium compound used during initiation is greater than the concentration of soluble chromium compound used during the production of the methyl formate.

* * * * *

UNITED STATES PATENT AND TRADEMARK OFFICE
CERTIFICATE OF CORRECTION

PATENT NO. : 4,851,569
DATED : July 25, 1989
INVENTOR(S) : DAVID J. DRURY et al

It is certified that error appears in the above-identified patent and that said Letters Patent is hereby corrected as shown below:

Col. 4, l. 63, should read "30 ml"

Col. 7, l. 18-19, there should be a comma after word "Example".

Col 7, l. 53, should read "30 ml"

Claim 5, line 1 should read ...according to claim 3 wherein...

Claim 8, line 1, change "9" to --7--

Signed and Sealed this

Twenty-second Day of May, 1990

*Attest:*

HARRY F. MANBECK, JR.

*Attesting Officer*  *Commissioner of Patents and Trademarks*